US010617658B2

(12) United States Patent
Colin et al.

(10) Patent No.: US 10,617,658 B2
(45) Date of Patent: Apr. 14, 2020

(54) USE OF HYDROXYCARBAMIDE FOR PREVENTING RETINAL NONPERFUSION

(71) Applicants: CENTRE HOSPITALIER NATIONAL D'OPHTALMOLOGIE QUINZE-VINGTS, Paris (FR); INSTITUT NATIONAL DE LA SANTE ET DE LA RECHERCHE MEDICALE (INSERM), Paris (FR); CENTRE NATIONAL DE LA RECHERCHE SCIENTIFIQUE (CNRS), Paris (FR); IMAGINE INSTITUT DES MALADIES GENETIQUES NECKER ENFANTS MALADES, Paris (FR); ASSISTANCE PUBLIQUE—HOPITAUX DE PARIS, Paris (FR); UNIVERSITE PARIS DESCARTES, Paris (FR)

(72) Inventors: Yves Colin, Vanves (FR); Jean-Francois Girmens, Paris (FR); Olivier Hermine, Paris (FR); Emmanuel Heron, Chatenay-malabry (FR); Michel Paques, Paris (FR)

(73) Assignees: CENTRE HOSPITALIER NATIONAL D'OPHTALMOLOGIE QUINZE-VINGTS, Paris (FR); INSTITUT NATIONAL DE LA SANTE DE LA RECHERCHE MEDICAL (INSERM), Paris (FR); CENTRE NATIONAL DE LA RECHERCHE SCIENTIFIQUE (CNRS), Paris (FR); IMAGINE INSTITUT DES MALADIES GENETIQUES NECKER ENFANTS MALADES, Paris (FR); ASSISTANCE PUBLIQUE—HOPITAUX DE PARIS, Paris (FR); UNIVERSITE PARIS DESCARTES, Paris (FR)

(*) Notice: Subject to any disclaimer, the term of this patent is extended or adjusted under 35 U.S.C. 154(b) by 0 days.

(21) Appl. No.: 15/750,143

(22) PCT Filed: Aug. 8, 2016

(86) PCT No.: PCT/EP2016/068908
§ 371 (c)(1),
(2) Date: Feb. 2, 2018

(87) PCT Pub. No.: WO2017/021560
PCT Pub. Date: Feb. 9, 2017

(65) Prior Publication Data
US 2018/0221313 A1 Aug. 9, 2018

(30) Foreign Application Priority Data
Aug. 6, 2015 (EP) .................... 15306277

(51) Int. Cl.
*A61K 31/17* (2006.01)
*A61P 27/02* (2006.01)
*A61P 9/14* (2006.01)

(52) U.S. Cl.
CPC ............... *A61K 31/17* (2013.01); *A61P 9/14* (2018.01); *A61P 27/02* (2018.01)

(58) Field of Classification Search
CPC ................................................. A61K 31/17
See application file for complete search history.

(56) References Cited

U.S. PATENT DOCUMENTS

| 6,462,071 | B1 | 10/2002 | Castillejos | |
| 7,008,960 | B1* | 3/2006 | Castillejos | ............. A61K 31/40 514/413 |
| 2008/0193499 | A1* | 8/2008 | Liu | ......... A61K 31/00 424/423 |
| 2014/0171504 | A1 | 6/2014 | Ganapathy | |

FOREIGN PATENT DOCUMENTS

WO 00/51620 A1 9/2000

OTHER PUBLICATIONS

Wautier et al., Red blood cell phosphatidylserine exposure is responsible for increased erythrocyte adhesion to endothelium in central retinal vein occlusion, First published: Mar. 1, 2011 https://doi.org/10.1111/j.1538-7836.2011.04251.x, Journal of Thrombosis and Haemostasis, 9: 1049-1055 (2011).*
Sanghvi et al., Superior macular sparing in central retinal artery occlusion due to sickle cell anaemia, Eye (2004) 18, 442-443.*
Liem et al., Sudden Onset Blindness in Sickle Cell Disease Due to Retinal Artery Occlusion, Pediatric blood and cancer, First published: Jan. 9, 2008, https://doi.org/10.1002/pbc.21152, vol. 50, issue 3, Mar. 2008, pp. 624-627.*
Pablo Bartolucci, et al., "Decreased sickle red blood cell adhesion to laminin by hydroxyurea is associated with inhibition of Lu/BCAM protein phosphorylation," Jun. 21, 2010; DOI 10.1182/blood-2009-12-257444.

(Continued)

*Primary Examiner* — Svetlana M Ivanova
(74) *Attorney, Agent, or Firm* — Arrigo, Lee, Guttman & Mouta-Bellum LLP (57) ABSTRACT

The present invention relates to the use of hydroxycarbamide (HC) for reducing and/or delaying the extension of capillary nonperfusion, a cause of irreparable visual impairment in patients suffering from central retinal vein occlusion (CRVO). This is the first systemic treatment which makes it possible to reduce retinal ischemic complications in patients in whom (CRVO) has been recently diagnosed and is consequently in a rapidly progressive phase. Given the low toxicity of HC evaluated on a large scale in children and adults in the context of other diseases for decades, the results of the present study open up a new therapeutic approach in the treatment of CRVO.

11 Claims, 2 Drawing Sheets

(56) References Cited

OTHER PUBLICATIONS

David M. Brown, et al., "Ranibizumab in Preproliferative (Ischemic) Central Retinal Vein Occlusion: The Rubeosis Anti-VEGF (RAVE) Trial," 2014;34:1728-35.

Jen-Tsan Chi, et al., "Endothelial cell diversity revealed by global expression profiling," PNAS, USA, vol. 100, No. 19, pp. 10623-10628 (2003).

Yves Colin, et al., "Red cell adhesion in human diseases," Curr Opin Hematol 2014, 21:186-192.

Elona Dhrami-Gavazi, et al., "Jak2 Mutation—Positive Polycythemia Vera Presenting as Central Retinal Artery Occlusion," Retinal Cases & Brief Reports, vol. 9, No. 2, pp. 127-130 (2015).

Jean P. Farcet, et al., "A Hypereosinophilic Syndrome With Retinal Arteritis and Tuberculosis," Arch. Intern. Med., vol. 142, pp. 625-627 (1982).

Julie Glanville, et al., "Efficacy and safety of widely used treatments for macular oedema secondary to retinal vein occlusion: a systematic review," BMC Ophthalmology 2014,14:7.

W. Richard Green, et al., "Central Retinal Vein Occlusion: A Prospective Histopathologic Study of 29 Eyes in 28 Cases," Tr. Am. Ophth. Soc. vol. LXXIX, 1981, pp. 371-422.

Sohan Singh Hayreh, et al., "Ocular Neovascularization Associated With Central and Hemicentral Retinal Vein Occlusion," Retina, The Journal of Retinal and Vitreous Diseases, 2012, vol. 32, No. 8, pp. 1553-1565.

Jennifer I. Lim, "Ophthalmic manifestations of sickle cell disease: update of the latest findings," Curr Opin Ophthalmol 2012, 23:533-536.

A. Pierre, et al., "Occlusions veineuses rétiniennes Retinal vein occlusion," EMC—Ophtalmologie, 21-240-E15, 2015.

Sophie Rogers, et al., "The Prevalence of Retinal Vein Occlusion: Pooled Data from Population Studies from the United States, Europe, Asia, and Australia," Ophthalmology. Feb. 2010 ; 117(2): 313-9.e1. doi:10.1016/j.3phtha.2009.07.017.

C. Sanghvi, et al., "Superior macular sparing in central retinal artery occlusion due to sickle cell anaemia," Eye (2004) 18, 442-443.

Stephen H. Sinclair, et al., "Prognosis for rubeosis iridis following central retinal vein occlusion," British Journal of Ophthalmology, 1979, 63, 735-743.

Michael Singer, et al., "Area of Peripheral Retinal Nonperfusion and Treatment Response in Branch and Central Retinal Vein Occlusion," Retina 2014;34:1736-42.

Richard F. Spaide, "Peripheral Areas of Nonperfusion in Treated Central REtinal Vein Occlusion as Imaged by Wide-Field Fluorescein Angiography," Retina 2011;31:829-37.

MH Steinberg, et al., "The Risks and Benefits of Long-term Use of Hydroxyurea in Sickle Cell Anemia: A 17.5 Year Follow-Up," Am J Hematol. Jun. 2010 ; 85(6): 403-408.

Irena Tsui, et al, "Ischemic Index and Neovascularization in Central Retinal Vein Occlusion," Retina 2011;31:105-10.

Ersi Voskaridou, et al., "The effect of prolonged administration of hydroxyurea on morbidity and mortality in adult patients with sickle cell syndromes: results of a 17-year, single-center trial (LaSHS)," Blood, Mar. 25, 2010 vol. 115, No. 12.

M.P. Wautier, et al., "Red blood cell phosphatidylserine exposure is responsible for increased erythrocyte adhesion to endothelium in central retinal vein occlusion," Journal of Thrombosis and Haemostasis, 9: 1049-1055.

Tom H Williamson, "A 'throttle' mechanism in the central retinal vein in the region of the lamina cribrosa," Br J Ophthalmol 2007;91:1190-1193.

Charles C. Wykoff, et al., "Progressive Retinal Nonperfusion in Ischemic Central Retinal Vein Occlusion," Retina 35:43-47, 2015.

* cited by examiner

USE OF HYDROXYCARBAMIDE FOR PREVENTING RETINAL NONPERFUSION

SUMMARY

The present invention relates to the use of hydroxycarbamide (HC) for reducing and/or delaying the extension of capillary nonperfusion, a cause of irreparable visual impairment in patients with central retinal vein occlusion (CRVO). This is the first systemic treatment for reducing retinal ischemic complications in patients in whom CRVO has been recently diagnosed and is consequently in a rapidly progressive phase. Given the low toxicity of HC evaluated on a large scale in children and adults in the context of other diseases for decades, the results of the present study open up a new therapeutic approach in the treatment of CRVO.

PRIOR ART

Retinal vein occlusion (RVO) includes central retinal vein occlusion (CRVO) and branch retinal vein occlusion (BRVO), the mechanisms, prognosis and treatments of which differ (Pierru A et al. EMC—*Ophtalmologie*, 21-240-E15, 2015). CRVO differs from BRVO by its more serious prognosis, the average age of onset (10 years lower), and the existence of familial cases. In physiopathological terms, BRVO occurs almost always at arteriovenous crossings (suggesting the involvement of a local process in the pathophysiology), whereas, in the case of CRVO, the location of venous obstruction is variable and its mechanism unknown. The prevalence of CRVO is about 5 times lower than that of BRVO.

CRVO is also distinguished from central retinal artery occlusion (CRAO), the latter generally resulting from cardiac or vascular embolism.

A meta-analysis of the epidemiologic data on RVO was published in 2010 (Rogers S. et al. Ophthalmology 2010; 117:313-9), with an estimate of average worldwide prevalence of CRVO of 0.8 per 1000, or 2.5 million people affected. CRVO is a serious disorder, responsible in more than 50% of patients for severe visual impairment, even blindness. Indeed, visual acuity <1/10 at 2 years is observed in about 50% of cases (80% if initial visual acuity is <1/10) (Pierru A et al. EMC—*Ophtalmologie*, 21-240-E15, 2015). Moreover, there is a risk of bilateral blindness related to this affection.

The most severe complication of CRVO is the appearance of retinal capillary nonperfusion, detected by the presence of an absence of capillary perfusion over a more or less extended area (see point D-1 in FIG. 2), leading to retinal ischemia, itself responsible not only for severe vision loss but, moreover, for neovascularization that can lead to glaucoma (Pierru A et al. EMC—*Ophtalmologie*, 21-240-E15, 2015). The mechanism by which capillary nonperfusion occurs is debated. The hypotheses put forth call upon endothelial cell edema, endothelial apoptosis, leukocyte obstruction, local thrombogenesis or hemorheological disorders (deformability and erythrocyte aggregation in particular). If few data are available with regard to variation in the area of nonperfusion, it has been shown that it is of the order of 25% on average during the first angiography (Singer M et al. Retina 2014; 34:1736-42). The area of retinal nonperfusion in these patients increases very quickly, by about 30% in the first 15 days of the disease (Singer M et al., Retina 2014; 34:1736-42; Spaide R F. Retina 2011; 31:829-37). Similarly, the complications of nonperfusion generally appear in the first months of progression of the CRVO (Sinclair S H et al. Br J Ophthalmol. 1979; 63:735-43; Hayreh S S et al. Retina 2012; 32:1553-65).

Despite the important place of CRVO in vascular pathology of the retina, its pathophysiology remains obscure, and very few risk factors have been identified.

In the past, it has been proposed to administer systemic antithrombotic treatments to CRVO patients. However, these treatments (aspirin, warfarin) have been shown to be ineffective, even harmful, in these patients (Pierru A et al. EMC—*Ophtalmologie*, 21-240-E15, 2015; Hayreh S S. et al. Ophthalmology 2011; 118:1603-1611). It appears today that, in CRVO patients, the acute occlusive phenomenon is not related to early thrombus formation, as fluorescence angiography shows a more or less marked slowing of venous flow without proper shutdown (Pierru A et al. EMC—*Ophtalmologie*, 21-240-E15, 2015), as the central retinal vein remains permeable to Doppler imaging (Williamson T H. Br J Ophthalmol 2007; 91:1190-1193), and as the presence of thrombus is not constantly described in the rare anatomopathological cases reported (Green W R et al. Retina 1981; 1:27-55).

No other systemic treatment has shown its efficacy in treating CRVO and symptoms thereof.

Most often, when CRVO is diagnosed, the therapeutic approach is limited to local administration (i.e., into the vitreous cavity of the eye) of anti-VEGF antibodies or corticoids and/or to local retinal photocoagulation (Glanville J et al. BMC Ophthalmol 2014; 14:7). Such local administration is painful for the patient, who must return to the hospital at regular intervals in order to undergo intravitreal injection. Moreover, this operation is invasive, since the needle must pass through the conjunctiva and the sclera in the ocular cavity located behind the crystalline lens. It can be performed only by a physician, under strictly controlled hygiene conditions, which restricts its access to patients who can travel to centers equipped for this operation. Moreover, this surgical procedure may generate potential complications: intraocular infection (which may occur, as in any puncture or surgical procedure, despite strict aseptic precautions), intraocular hypertonia (increased intraocular pressure), accidental damage to the crystalline lens, or retinal detachment.

Moreover, although relatively effective for suppressing neovascularization, none of these local treatments prevents the extension of the area of retinal nonperfusion, which is the cause of retinal ischemia and the blinding complications thereof (macular degeneration, neovascularization, retinal/intravitreal hemorrhage, neovascular glaucoma). It was recently observed, for example, that the area of retinal nonperfusion increases by about 30% during the first 3 months in cases of ischemic CRVO, even if the patient is treated locally with anti-VEGF (Wykoff C C et al. Retina 2015; 35:43-7). Anti-VEGF injections have only a "suspensive" effect, as neovascularization may then occur once the injections are stopped (Brown D M et al. Retina 2014; 34:1728-35).

The visual loss sustained by patients suffering from CRVO with retinal ischemia is thus regarded today as irreversible, as no case of spontaneous reperfusion (even localized) of retinal capillary occlusion has been documented to date.

In this context, it has become urgent to identify a noninvasive and effective treatment for purposes of treating CRVO patients, in order to relieve the symptoms related to this pathology and, more precisely, to prevent the extension of the area of retinal nonperfusion, responsible for the retinal atrophy observed in these patients.

DESCRIPTION OF THE INVENTION

Figure 1:
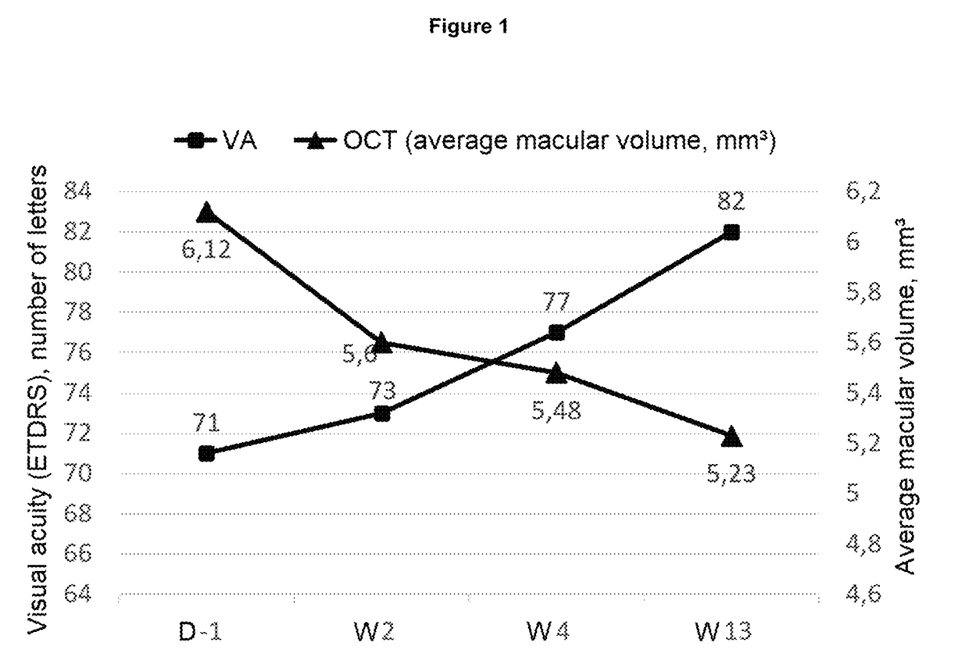
FIG. 1 shows the visual acuity (VA) and the average macular volume (OCT) of the patient the day before treatment (D-1), as well as 15 days after initiation of treatment (W2), 27 days after initiation of treatment (W4) and 107 days after initiation of treatment (W13).
Figure 2:
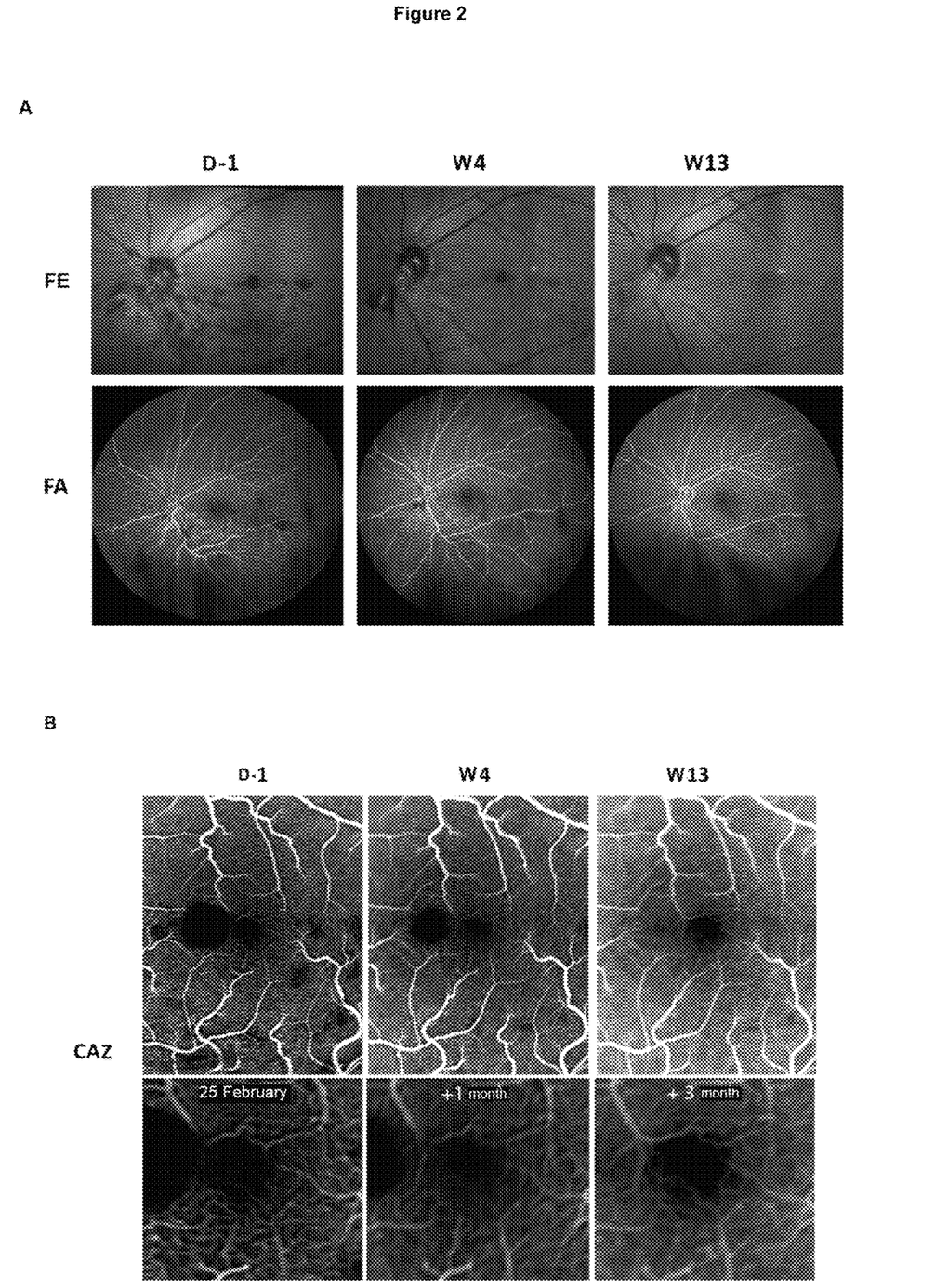
FIG. 2 shows (A) the fundus of the eye (FE), the retinal fluorescein angiography (FA) and (B) the angio-OCT showing the area of the central avascular zone (CAZ) the day before treatment (D-1), as well as 27 days after initiation of treatment (W4) and 107 days after initiation of treatment (W13).

The present inventors demonstrate herein that it is possible to significantly reduce the extension of the area of retinal nonperfusion by administering to CRVO patients, and notably those with CRVO that has been diagnosed recently (i.e., within one month) and thus is in full progression, an initial dose of 20 mg/kg/day of hydroxycarbamide (HC) via the oral route (FIGS. 1 and 2).

The study presented below demonstrates, by various clinical indicators, that the area of retinal nonperfusion is stabilized after a few weeks of such treatment (Results and FIGS. 1 and 2).

Thus, the present patent application concerns, in a first aspect, hydroxycarbamide for use in treating CRVO patients via the systemic route.

More precisely, hydroxycarbamide can be used, in these patients, to:
- prevent or delay the increase in the area of peripheral retinal capillary nonperfusion (measurable by widefield angiography, which makes it possible to measure a "nonperfusion index" (ISI), which when <45% indicates a very low risk of neovascularization (Tsui I. et al. Retina 2011; 31:105-10), notably in the first weeks when the disease actively progresses,
- prevent or delay the appearance of indirect signs of retinal ischemia (iris collarette reperfusion, rubeosis iridis, neovascular glaucoma, abolished afferent pupillary response, measurable by biomicroscopic examination of the anterior segment of the eye),
- reduce macular thickness by 100 µm, preferably by 200 µm, more preferably by 300 µm after 3 months of treatment, and/or
- avoid or inhibit loss of visual acuity (loss of more than 15 letters/3 lines on the ETDRS scale).

Hydroxycarbamide (HC) (chemical formula: $CH_4N_2O_2$, a hydroxylated analogue of urea—also called hydroxyurea or HU) was synthesized in Germany in 1869 by Dressler and Stein, but it was only in 1928 that it was administered to animals in which leukopenia, macrocytosis and anemia type blood abnormalities were observed. It was necessary to wait until 1963 for Stearns et al. to show that hydroxycarbamide can be active against mouse L1210 leukemia, then thereafter many clinical studies demonstrated its anti-tumor action in humans. Some of these studies showed its efficacy in treating solid tumors such as malignant melanoma, refractory ovarian cancer, head and neck carcinoma, renal or vesical carcinoma. But the appearance of new, more effective treatments for these tumors and the low response rate have today relegated HC behind other lines of treatment and always in combination with other chemotherapies.

Today, however, HC remains fully relevant in the therapeutic management of:
- Myeloproliferative syndromes such as polycythemia vera (PV), essential thrombocythemia (ET), myeloid splenomegaly and chronic myeloid leukemia (the medicinal product Hydrea® is administered in this case).

HC is a specific inhibitor of the S phase of the cell cycle. It inhibits ribonucleotide reductase (RR), which transforms ribonucleotides into deoxyribonucleotides. When inhibited, this enzyme, which is produced in very small amounts, causes a decrease in the production of DNA precursors. This effect is dose-dependent and also correlated with exposure time to the medicinal product in most mammalian cell cultures with no major secondary effect. This property is the one chiefly sought in the treatment of myeloproliferative syndromes.

- Prevention of vaso-occlusive crises and acute thoracic syndrome in symptomatic sickle-cell disease (the medicinal product Siklos® is administered in this case).

HC is today the only active ingredient that modifies the course of sickle-cell disease. The 17.5-year follow-up of the MSH study published by Steinberg et al. (Steinberg M H et al., Am J Hematol. 2010; 85:403-8) shows that patients who received HC treatment have a 40% lower death rate than patients who did not receive HC. Furthermore, Voskaridou et al. (Blood 2010; 115:2354-63) report the 17-year follow-up of a prospective study involving 330 patients. Among these patients, 131 received HC while 199 were conventionally treated with analgesics, hydration, or oxygen therapy. The probability of 10-year survival was 86% and 65% for HC and non-HC patients, respectively ($p=0.001$), and this despite the fact that patients treated with HC had more severe forms of sickle-cell disease.

Sickle-cell patients do not develop CRVO, although other retinal vascular complications have been observed in these patients (see Lim J I et al. Curr Opinion Ophthalmol 2012; 23:533-6). Similarly, myeloproliferative syndrome patients do not develop CRVO.

Two phenomena (at least) can explain these observations:

First, red blood cells (RBCs) of CRVO patients do not exhibit the same abnormalities as RBCs of sickle-cell or myeloproliferative syndrome patients. In particular, most adhesion molecules are normally expressed on the surface of RBCs of CRVO patients (Wautier M P et al. J Thromb Haemost 2011; 9:1049-55), which is not the case for RBCs of sickle-cell or myeloproliferative syndrome patients (Colin Y et al. Curr Opin Hematol 2014; 21:369).

Second, microcirculatory endothelial cells from different tissues have been described as having distinct and characteristic gene and protein expression profiles (Chi J T et al. PNAS 2003; 100:10623-8).

Preferably, the patients treated (or to be treated) in the context of the invention have CRVO alone. In particular, they do not have, in addition to CRVO, a myeloproliferative syndrome. Moreover, they do not have, in addition to CRVO, sickle-cell disease. Lastly, in a general manner, they do not have any serious and progressive general illness, such as cancer (solid or leukemia).

By "myeloproliferative syndrome" is meant, within the meaning of the present invention, the following diseases: polycythemia vera (PV), essential thrombocythemia (ET), myeloid splenomegaly, chronic myeloid leukemia (CML).

In particular, the patients treated (or to be treated) in the context of the invention do not have essential thrombocythemia.

By "cancer" is meant, within the meaning of the invention, any type of solid cancer (such as malignant melanoma, refractory ovarian cancer, head and neck carcinoma, renal or vesical carcinoma) or blood cancer (such as leukemia).

In particular, the patients treated (or to be treated) in the context of the invention do not have glaucoma.

Moreover, the patients treated (or to be treated) in the context of the invention are preferably adults (men or women) at least 45 years of age. Because of the very low toxicity of HC, including in older patients, there is no maximum age to be treated with the treatment of the invention.

Preferably, the patients treated (or to be treated) in the context of the invention have been diagnosed with CRVO within the previous month. In other words, said patient's CRVO symptoms appeared within the previous month, before said administration. The area of retinal nonperfusion in these patients increases very quickly during this period, by about 30% in 15 days, which can lead to retinal ischemia and, in the long term, blindness (Singer M et al. Retina 2014; 34:1736-42; Spaide R F et al. Retina 2011; 31:829-37).

The diagnosis of CRVO is traditionally made by conventional ophthalmological examinations, performed in an ophthalmologist's office or in a hospital. It is based on examination of the fundus of the eye. Certain additional explorations (retinal angiography, optical coherence tomography (OCT)) may be necessary to evaluate its effects.

More precisely, the patients treated (or to be treated) in the context of the invention will have been selected because they have the following symptoms:
  Loss of visual acuity for less than one month,
  Presence in the examination of the fundus of the eye of the signs characteristic of CRVO:
    Retinal hemorrhages scattered in all four quadrants,
    Venous dilation and tortuosity,
    If fluorescein angiography was performed: delayed venous filling.

The diagnosis of CRAO, which is most often due to embolism, is also made in a traditional manner by conventional ophthalmological examinations, which may be performed in an ophthalmologist's office or in a hospital. It is based on examination of the fundus of the eye.

However, unlike CRVO, CRAO patients have the following symptoms:
  Very sudden (1 sec) loss of visual acuity and total loss of visual field;
  Mydriasis of the affected eye;
  Examination of the fundus of the eye through dilated pupils to establish:
    a disappearance of small arteries,
    an edema of the posterior pole of the eye,
    a macula having a "cherry-red" type color.

The treatment of the invention is such that a dose ranging between 12.5 and 25 mg/kg/day, preferably 20 mg/kg/day of hydroxycarbamide is administered to said patients. These doses correspond to the doses used in myeloproliferative syndromes as well as in sickle-cell disease. At these doses, very few adverse effects were reported in both adults and children.

The administered dose may vary in the following cases:
  1—in the case of absence of mean corpuscular volume increase (increase <10%) after the first month of treatment, the dose of HC may be increased by 2.5 mg/kg/d.
  2—in the case of toxicity (greater than 20% decrease in hemoglobin in relation to baseline hemoglobin, and/or reticulocytes <80,000/mm$^3$, and/or polymorphonuclear neutrophils <2000/mm$^3$, and/or platelets <80,000/mm$^3$), the treatment may be temporarily stopped and then recommenced at a dose 2.5 mg/kg/d lower than the previous dose. In the case of recurrent toxicity at a dose lower than 15 mg/kg/d, the treatment must be definitely abandoned.

The administration of HC is preferably via the oral route, which makes it easy, fast and safe for the patient. Advantageously, this mode of administration makes it possible to avoid the intervention of a health professional, unlike the local treatments currently used.

The present invention thus concerns the use of HC to prepare a pharmaceutical composition (or a medicinal product) for treating CRVO patients (as defined above) via the systemic route, more precisely, for preventing or delaying the increase in the area of retinal capillary nonperfusion, for preventing or delaying the appearance of indirect signs of retinal ischemia, for maintaining the macular thickness (or reducing it in the case of macular edema), and/or for maintaining the vision in these patients.

More precisely, said composition will be for preventing, delaying or even avoiding the increase in the area of retinal capillary nonperfusion such that the area does not increase by more than 30%, preferably by more than 20%, more preferably by more than 10%, in relation to the area of retinal capillary nonperfusion before treatment.

Furthermore, said composition will be for preventing, delaying or even avoiding the loss of visual acuity such that said loss remains less than 15 letters on the ETDRS scale, preferably less than 10 letters on the ETDRS scale.

Lastly, said composition will be for reducing the ocular macular thickness by 100 µm, preferably by 200 µm, more preferably by 300 µm after 3 months of treatment.

The present invention also concerns a pharmaceutical composition that can be administered via the systemic route (preferably via the oral route), for use in preventing or treating patients with CRVO (as defined above), more precisely, in preventing or delaying the increase in the area of peripheral retinal capillary nonperfusion, in preventing or delaying the appearance of indirect signs of retinal ischemia, in maintaining the macular thickness, and/or in maintaining the vision in these patients.

This pharmaceutical composition contains, in addition to HC, at least one pharmaceutically acceptable excipient.

By "pharmaceutically acceptable excipient" is meant herein a compound or a combination of compounds that does not cause secondary reactions and that, for example, facilitates administration of the active compound, increases the lifespan and/or the efficacy thereof in the organism, increases the solubility in solution thereof or improves the preservation thereof. Said pharmaceutically acceptable excipients are well-known and will be adapted by persons skilled in the art as a function of the nature and the mode of administration of the active compound(s) selected.

The dosage form of said composition is preferably a form that can be administered via the oral route, for example a tablet, a capsule, a powder, a granule, a solution or an oral suspension (syrup) or any sublingual and buccal administration form.

When a solid composition is prepared in tablet form, the active ingredient (HC) can be mixed with a pharmaceutical excipient such as gelatin, starch, lactose, magnesium stearate, talc, gum arabic or the like. Said tablets may be coated with sucrose or other suitable substances or may be treated such that they have extended or delayed activity and that they continuously release a predetermined amount of HC.

Capsules are obtained, for example, by mixing the active ingredient (HC) with a diluent and pouring the mixture obtained into soft or hard capsules.

A preparation in syrup or elixir form may contain the active ingredient (HC) together with a sweetener, an antiseptic, as well as a flavoring agent and/or a suitable dye.

Water-dispersible powders or granules may contain the active ingredient (HC) optionally mixed with dispersants, wetting agents, suspension agents, with flavor enhancers and/or sweeteners.

For example, it is possible to treat said patients using Siklos 1000 mg tablets containing, in addition to 1000 mg of hydroxycarbamide, sodium stearyl fumarate, silicified microcrystalline cellulose and basic butylated methacrylate copolymer. It is also possible to treat said patients using Hydrea 500 mg tablets containing, in addition to 500 mg of hydroxycarbamide, sodium hydrogen phosphate, citric acid, lactose and magnesium stearate.

Preferably, the pharmaceutical composition of the invention is taken on an empty stomach, more preferably in the morning before breakfast.

Preferably, said composition is taken every day for at least six months.

The present invention thus concerns a method for preventing or treating patients with CRVO (as defined above), more precisely, for preventing or delaying the increase in the area of peripheral retinal capillary nonperfusion, for preventing or delaying the appearance of indirect signs of retinal ischemia, for reducing the macular thickness in the case of macular edema, and/or for maintaining the vision in these patients, said method comprising the step of administering to said patient, via the systemic route, an effective amount of a pharmaceutical composition as defined above, containing hydroxycarbamide.

EXAMPLES

1. Patients Examined in the Study

Patients enrolled in the study are at least 45 years of age, of both sexes, presenting with CRVO, the symptoms of which appeared less than one month before receiving care and included a loss of visual acuity with corrected visual acuity of the affected eye less than 6/10 (73 ETDRS letters).

Patients not meeting these criteria are not included in the study. Also excluded are patients:
- Having vision in only one eye (whose contralateral visual acuity is less than 4/10)
- Having a history of trauma or of oculo-orbital surgery in the 6 months preceding the first ophthalmologic clinical manifestations,
- Having a history of cephalic radiotherapy,
- With a tumor of the orbit or of the optic nerve homolateral to the RVO,
- With contralateral vascular retinal pathology, in particular moderate diabetic retinopathy (the minimal stage not being a contraindication),
- With ocular neovascularization (including rubeosis iridis),
- With a contraindication for pupil dilation (including tropicamide allergy),
- Allergic to fluorescein, or to HC,
- With a progressive local or general inflammatory pathology,
- With sickle-cell disease,
- With a known myeloproliferative syndrome,
- With signs of myelosuppression: hemoglobin <13 g/dL (men) or <12 g/dL (women), reticulocytes <20,000/mm$^3$, polymorphonuclear neutrophils <1500/mm$^3$, platelets <150,000/mm$^3$
- Being treated with hydroxycarbamide before inclusion in the protocol,
- Being treated with anticoagulant before inclusion in the protocol,
- With renal insufficiency with creatinine clearance ≤60 mL/min,
- With severe hepatic insufficiency (Child-Pugh C class),
- Women who are pregnant, nursing or not using contraception,
- Men desiring to become fathers.

2. Protocol for Follow-Up and for Administration of the Medicinal Product

Between D0-10 and D0 or D0-20 and D0: a physician verifies all the eligibility and ineligibility criteria for the protocol, collects the patient's complete clinical notes, and gives the patient a detailed and interactive oral briefing on the study, as well as the information leaflet and the consent form.

Blood tests (CBC and serum creatinine measurements) are also carried out. These tests, which are part of the common CRVO assessment, are used to confirm the absence of biological criteria for non-inclusion in the study.

D0 is the day the patient is included in the study. That same day, after the patient has signed a written consent form, the following tests are performed:
- Blood samples (CBC-reticulocytes, ESR, CRP, PT, PTT, fibrin, protein electrophoresis, serum creatinine, lipid profile, fasting glucose, HbA1c). For these various tests, the patient is fasting.
- Specialized ophthalmological examinations (retinal angiography, OCT).

The patient also receives the hydroxycarbamide tablets enabling him or her to carry out the first part of the treatment. The first treatment dose must be taken by the patient as of the following morning (D1), on an empty stomach. The treatment must then be taken daily, preferably on an empty stomach.

The dosage form used in the present study is the oral form Siklos marketed by Addmedica in France. This medicinal product was granted a European MA on 28 Jun. 2007 for the proprietary product Siklos 1000 mg film-coated tablets for the prevention of recurrent painful vaso-occlusive crises including acute chest syndrome in adults, adolescents and children older than 2 years suffering from symptomatic sickle-cell syndrome. It is an oblong, white, film-coated, triple-scored tablet that can be divided into 4 equal 250-mg parts. These tablets are provided in a high-density polyethylene (HDPE) bottle containing 30 tablets with a polypropylene (PP) child-resistant closure with a desiccant unit. It must be stored in a location where the temperature does not exceed 30° C., for a maximum of 24 months. Each 1000 mg Siklos tablet contains 1000 mg of hydroxycarbamide. The qualitative composition of Siklos 1000 mg is hydroxycarbamide, sodium stearyl fumarate, silicified microcrystalline cellulose and basic butylated methacrylate copolymer.

According to the protocol, the patient must swallow the equivalent of 20 mg/kg of the Siklos tablet every day for one month. The table below indicates the dose and the number of Siklos tablets to be taken as a function of the patient's body weight.

TABLE

Hydroxycarbamide dosage as a function of the patient's weight

| weight in kg | 15 mg/kg/d | 17.5 mg/kg/d | 20 mg/kg/d | 22.5 mg/kg/d | 25 mg/kg/d |
| --- | --- | --- | --- | --- | --- |
| 45 | 675 | 787.5 | 900 | 1012.5 | 1125 |
| 46 | 690 | 805 | 920 | 1035 | 1150 |
| 47 | 705 | 822.5 | 940 | 1057.5 | 1175 |

TABLE-continued

Hydroxycarbamide dosage as a function of the patient's weight

| weight in kg | 15 mg/kg/d | 17.5 mg/kg/d | 20 mg/kg/d | 22.5 mg/kg/d | 25 mg/kg/d |
|---|---|---|---|---|---|
| 48 | 720 | 840 | 960 | 1080 | 1200 |
| 49 | 735 | 857.5 | 980 | 1102.5 | 1225 |
| 50 | 750 | 875 | 1000 | 1125 | 1250 |
| 51 | 765 | 892.5 | 1020 | 1147.5 | 1275 |
| 52 | 780 | 910 | 1040 | 1170 | 1300 |
| 53 | 795 | 927.5 | 1060 | 1192.5 | 1325 |
| 54 | 810 | 945 | 1080 | 1215 | 1350 |
| 55 | 825 | 962.5 | 1100 | 1237.5 | 1375 |
| 56 | 840 | 980 | 1120 | 1260 | 1400 |
| 57 | 855 | 997.5 | 1140 | 1282.5 | 1425 |
| 58 | 870 | 1015 | 1160 | 1305 | 1450 |
| 59 | 885 | 1032.5 | 1180 | 1327.5 | 1475 |
| 60 | 900 | 1050 | 1200 | 1350 | 1500 |
| 61 | 915 | 1067.5 | 1220 | 1372.5 | 1525 |
| 62 | 930 | 1085 | 1240 | 1395 | 1550 |
| 63 | 945 | 1102.5 | 1260 | 1417.5 | 1575 |
| 64 | 960 | 1120 | 1280 | 1440 | 1600 |
| 65 | 975 | 1137.5 | 1300 | 1462.5 | 1625 |
| 66 | 990 | 1155 | 1320 | 1485 | 1650 |
| 67 | 1005 | 1172.5 | 1340 | 1507.5 | 1675 |
| 68 | 1020 | 1190 | 1360 | 1530 | 1700 |
| 69 | 1035 | 1207.5 | 1380 | 1552.5 | 1725 |
| 70 | 1050 | 1225 | 1400 | 1575 | 1750 |
| 71 | 1065 | 1242.5 | 1420 | 1597.5 | 1775 |
| 72 | 1080 | 1260 | 1440 | 1620 | 1800 |
| 73 | 1095 | 1277.5 | 1460 | 1642.5 | 1825 |
| 74 | 1110 | 1295 | 1480 | 1665 | 1850 |
| 75 | 1125 | 1312.5 | 1500 | 1687.5 | 1875 |
| 76 | 1140 | 1330 | 1520 | 1710 | 1900 |
| 77 | 1155 | 1347.5 | 1540 | 1732.5 | 1925 |
| 78 | 1170 | 1365 | 1560 | 1755 | 1950 |
| 79 | 1185 | 1382.5 | 1580 | 1777.5 | 1975 |
| 80 | 1200 | 1400 | 1600 | 1800 | 2000 |
| 81 | 1215 | 1417.5 | 1620 | 1822.5 | 2025 |
| 82 | 1230 | 1435 | 1640 | 1845 | 2050 |
| 83 | 1245 | 1452.5 | 1660 | 1867.5 | 2075 |
| 84 | 1260 | 1470 | 1680 | 1890 | 2100 |
| 85 | 1275 | 1487.5 | 1700 | 1912.5 | 2125 |
| 86 | 1290 | 1505 | 1720 | 1935 | 2150 |
| 87 | 1305 | 1522.5 | 1740 | 1957.5 | 2175 |
| 88 | 1320 | 1540 | 1760 | 1980 | 2200 |
| 89 | 1335 | 1557.5 | 1780 | 2002.5 | 2225 |
| 90 | 1350 | 1575 | 1800 | 2025 | 2250 |
| 91 | 1365 | 1592.5 | 1820 | 2047.5 | 2275 |
| 92 | 1380 | 1610 | 1840 | 2070 | 2300 |
| 93 | 1395 | 1627.5 | 1860 | 2092.5 | 2325 |
| 94 | 1410 | 1645 | 1880 | 2115 | 2350 |
| 95 | 1425 | 1662.5 | 1900 | 2137.5 | 2375 |
| 96-100 | 1440 | 1680 | 1920 | 2160 | 2400 |

Patients are advised to take the medicinal product preferably in the morning before breakfast (on an empty stomach), if needed with a small amount of water or food. For patients unable to swallow the tablets, the tablets may be dissolved in a little water in a teaspoon immediately before consumption.

At D15 (W2), D30 (W4), D45, D60 and at M3 (W13), M4, M5 and M6 (W26): a hematological profile (CBC, reticulocytes) is prepared, to monitor the hematological tolerance of the treatment.

Follow-up visits take place at D15 (W2), M1 (W4), M3 (W13) and M6 (W26) (D15: 14±2, M1: 28±2, M3: 91±20 days, M6: 182±2 days after initiation of treatment). They comprise an ophthalmological examination, an internal medicine consultation, blood sampling at the laboratory, and a visit to the pharmacy where the treatment taken is recorded and the following batch is delivered.

The main objective of the three physician visits at M1 (W4), M3 (W13) and M6 (W26) is to evaluate treatment compliance and tolerance during the study.

The efficacy of the treatment with regard to the prevention of retinal nonperfusion is evaluated at D15 (W4), M1 (W13) and M6 (W26). The effect of the treatment on visual acuity and on macular thickness is evaluated at D15 (W2), M1 (W4), M3 (W13) and M6 (W26). At M6 (W26), the incidence of rubeosis iridis and of neovascular glaucoma is evaluated.

The efficacy of the treatment on the biological parameters of the research, in particular the in vitro hemorheological parameters, is evaluated at D15 (W2), M1 (W4), M3 (W13) and M6 (W26), and spontaneous erythroid colony formation is tested at M3 (W13).

A change in dose is made in the following cases:
1—in the case of absence of mean corpuscular volume increase (increase <10%) after the first month of treatment, the dose of HC was increased by 2.5 mg/kg/d.
2—in the case of toxicity (greater than 20% decrease in hemoglobin in relation to baseline hemoglobin, and/or reticulocytes <80,000/mm$^3$, and/or polymorphonuclear neutrophils <2000/mm$^3$, and/or platelets <80,000/mm$^3$), the treatment is temporarily stopped and then recommenced at a dose 2.5 mg/kg/d lower than the preceding dose. In the case of recurrent toxicity at a dose lower than 15 mg/kg/d, the treatment is definitely abandoned.

3. Tests Performed

The blood test carried out at D0 comprises the measurement of: CBC-reticulocytes, ESR, CRP, PT, PTT, fibrin, protein electrophoresis, serum creatinine, lipid profile, fasting glucose, HbA1c.

This test aims to eliminate the presence of possible blood disease, in particular myeloproliferative syndrome, as well as possible hepatic or severe renal insufficiency, all of which constitute criteria for non-inclusion in the study. It also aims to specify the patient's vascular risk factors, notably diabetes and dyslipidemia.

The same day (at D0), the patients undergo a complete ophthalmological evaluation, comprising retinal fundus photography, ETDRS visual acuity, angiography and OCT examination.

The ophthalmological examinations performed in the context of this study are part of the routine exploration of CRVO.

The photographs taken of the fundus of the eye (fundus photography) are used to create an archive document.

Fluorescein angiography is carried out with a Spectralis scanning laser ophthalmoscope (SLO) (Heidelberg Engineering, Heidelberg, Germany), equipped with an "ultra-wide-field" objective (UWF 102). During the actual imaging, the patient, whose pupil has first been dilated, is asked to place his or her head on a chin strap. Once the unit is focused, fluorescein is injected intravenously. The fundus of the eye is continuously scanned to detect the appearance of fluorescein in the retinal arteries. Once fluorescein appears in the retinal arteries, a high-resolution video recording is made of the entire period of vascular filling (10 seconds on average). Once arteriovenous filling is complete, a photograph at the highest magnification, centered on the central avascular zone (CAZ), is taken (in both eyes), then the remainder of the angiography is continued in wide-field mode. The area of nonperfusion is measured manually using the measuring instruments of the Spectralis apparatus, by calculating the ratio of the nonperfused area to the total retinal area.

OCT comprises two cross-sections (horizontal and vertical) centered on the fovea, as well as macular mapping. Angio-OCT is also carried out using the Optovue® apparatus to evaluate the foveal capillary network without injection. The area of the central avascular zone (CAZ) is then measured using the software tools provided by the manufacturer.

The standardized measurement of visual acuity using the ETDRS scale, which is internationally recognized and validated, is performed by an orthoptist (duration about 30 minutes). This measurement is performed at each patient visit during the study.

As fluorescein angiography sometimes contributes little or is difficult to interpret, the progression of retinal perfusion is evaluated not only by angiography (change in the area of nonperfused retina and of the central avascular zone), but also by investigating the appearance of clinical signs secondary to retinal ischemia: abolished afferent pupillary response, iris vessel dilation, iris collarette reperfusion, appearance of iris neovascularization, in the iridocorneal angle or preretinal, or even the appearance of neovascular glaucoma.

Tests are also performed in order to understand the mechanism of action of HC on retinal capillaries. In particular, circulating hematopoietic progenitors are taken (2*5 mL tubes on EDTA) at D0 then at M3 (W13) for patients having endogenous erythroid colonies at inclusion. The rheological properties of red blood cells are analyzed on a LoRRca MaxSis Osmoscan ektacytometer (Mechatronics) and a Brookfield viscometer. Several characteristics are studied: blood viscosity, overall red blood cell aggregation in the patients' plasma, and also stability and membrane deformability characteristics.

4. Results

After analysis of the ophthalmic tests described above, the treatment success rate is proportional to the percentage of patients in which none the following events was observed three months after initiation of treatment:

Greater than 30% increase in the area of peripheral nonperfusion measured by wide-field angiography, Appearance of indirect signs of retinal ischemia: iris collarette reperfusion, rubeosis iridis, neovascular glaucoma, decreased afferent pupillary response.

Furthermore, blood tests are important in order to control the hematological tolerance of the treatment.

The results of the clinical study below show that it is possible to reduce the increase in the area of retinal nonperfusion by administering HC via the oral route under the study conditions. Moreover, oral treatment with HC at the doses used appears minimally toxic, which is consistent with the previous clinical studies carried out with this treatment.

Clinical Study

The case of a 60-year-old Caucasian man with a long-standing history of cat-scratch disease and of erysipelas on the left leg, with no vascular risk factor and without chronic treatment, having presented to the eye emergency department for metamorphopsia and blurred vision in the left eye lasting for 24 h, and receiving the treatment in accordance with the protocol presented above, was followed as described below.

The initial ophthalmological examination of the patient revealed left visual acuity of 10/10f P2 and intraocular pressure of 15 mmHg, with at the fundus of the eye an inferior hemi-central retinal vein occlusion, with venous dilation and tortuosity, hemorrhages and cotton-wool spots.

Thirteen days after his first visit, the ophthalmological examination revealed visual acuity of the left eye of 5/10f P2 and intraocular pressure of 16 mmHg. Optical coherence tomography (OCT) showed macular edema and juxtafoveal hemorrhage.

Nineteen days after his first visit (D-1 of treatment), visual acuity measured on the ETDRS scale was 71 letters for the left eye and 89 letters for the right eye. Retinal fluorescein angiography confirmed the diagnosis of edematous CRVO by finding a slowing of inferior hemi-vein circulation and an absence of a nonperfusion zone. OCT-angiography made it possible to evaluate the area of the central avascular zone (CAZ) equal to 0.12 mm$^2$. The average central thickness of the retinal surface was equal to 316 µm and the average macular volume equal to 6.12 mm$^3$ (FIGS. 1 and 2, D-1).

Hydroxycarbamide treatment is started the following day in the form of 1750 mg per day (20 mg/kg/day) of Siklos orally.

The follow-up visits took place 13 days (W2/D15), 27 days (W4/M1) and 108 days (W13/M3) after initiation of treatment. Hydroxycarbamide was stopped for 3 days (just after the W4/M1 visit) due to thrombocytopenia at 60,000/mm$^3$, then recommenced at the dose of 17.5 mg/kg/d. It was stopped again 1 week later for 16 days due to a greater than 20% decrease in hemoglobin in relation to pre-treatment hemoglobin, then recommenced at the dose of 15 mg/kg/d until the W13/M3 visit. Clinical tolerance of the treatment was perfect and changes in blood count were asymptomatic.

At the W2 visit, visual acuity (ETDRS scale) of the left eye was measured at 73 letters for the left eye (FIG. 1). During examination of the fundus of the left eye a reduction in hemorrhages was noted. OCT showed an average central retinal thickness of 300 µm and an average macular volume of 5.6 mm$^3$.

At the W4 post-treatment initiation visit, visual acuity (ETDRS scale) of the left eye was measured at 77 letters for the left eye (FIG. 1). During examination of the fundus of the left eye a reduction in hemorrhages, as well as in inferior venous caliber and tortuosity, was noted (FIG. 2A). OCT showed an average central retinal thickness of 293 µm and an average macular volume of 5.48 mm$^3$ (FIG. 1). Retinal fluorescein angiography found an improvement in circulation times in the inferior hemi-vein with the appearance of papillary collateral and confirmed the absence of a nonperfusion zone (FIG. 2A). By OCT-angiography, the area of the central avascular zone (CAZ) was evaluated at 0.10 mm$^2$ (FIG. 2B).

At the W13 post-treatment initiation visit, left visual acuity was measured at 82 letters (ETDRS; FIG. 1). During examination of the fundus of the left eye a disappearance of hemorrhages, a near-normal inferior venous caliber and the presence of papillary collateral circulation were noted (FIG. 2A). By OCT, the macular profile was substantially normal, with an average macular volume of 5.23 mm$^3$ (FIG. 1). The average central retinal thickness was 281 µm. Retinal fluorescein angiography found a normalization of circulation times in the inferior hemi-vein and confirmed the absence of a nonperfusion zone (FIG. 2A). OCT-angiography made it possible to evaluate the area of the central avascular zone (CAZ) equal to 0.09 mm$^2$ (FIG. 2B).

In conclusion, in this 60-year-old patient with hemi-vein occlusion, under treatment with hydroxycarbamide, the following were observed: improved circulation in the inferior hemi-vein and development of collateral circulation, normalization of venous caliber and of the FE with disappearance of hemorrhages and reduced macular edema allowing improved visual acuity (+11 ETDRS letters). A moderate reduction in average central retinal thickness (35 µm reduction) was also observed, the edema not being central in this patient. Importantly, the peripheral retina was always well perfused during treatment and there was no significant change in the area of the CAZ.

The invention claimed is:

1. A method of reducing and/or delaying the increase of capillary nonperfusion area in a patient suffering from central retinal vein occlusion (CRVO), comprising systemically administering daily for a treatment period of at least one month a composition consisting essentially of Hydroxycarbamide (HC) to said patient, wherein said patient does not suffer from a myeloproliferative syndrome, and wherein said patient does not suffer from a sickle-cell disease.

2. The method of claim 1, wherein said patient is a person at least 45 years of age.

3. The method of claim 1, wherein administration of HC is initiated within one month of onset of CRVO symptoms.

4. The method of claim 1, wherein said HC is administered at a dose of 20 mg/kg/day.

5. The method of claim 1, wherein said HC is administered orally.

6. The method of claim 1, wherein the area of capillary nonperfusion in said patient increases by less than 30% during the treatment period.

7. The method of claim 1, wherein the area of capillary nonperfusion in said patient increases by less than 20% during the treatment period.

8. The method of claim 1, wherein the area of capillary nonperfusion in said patient increases by less than 10% during the treatment period.

9. The method of claim 1, wherein said patient does not experience a loss of visual acuity.

10. The method of claim 1, wherein said treatment period is at least three months and said patient experiences a reduction of macular thickness of at least 100 μm after 3 months of treatment.

11. The method of claim 1, wherein the area of capillary nonperfusion in said patient does not increase during the treatment period.

* * * * *